(12) United States Patent
Kusaka

(10) Patent No.: US 10,493,560 B2
(45) Date of Patent: Dec. 3, 2019

(54) OPTICAL DEVICE AND LASER PROCESSING APPARATUS

(71) Applicant: Kabushiki Kaisha Toshiba, Minato-ku (JP)

(72) Inventor: Tsubasa Kusaka, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 533 days.

(21) Appl. No.: 15/259,503

(22) Filed: Sep. 8, 2016

(65) Prior Publication Data

US 2017/0072506 A1    Mar. 16, 2017

(30) Foreign Application Priority Data

Sep. 10, 2015    (JP) ................. 2015-178598

(51) Int. Cl.
| | |
|---|---|
| B23K 26/03 | (2006.01) |
| G02B 27/14 | (2006.01) |
| G02B 17/08 | (2006.01) |
| G01N 21/88 | (2006.01) |
| B23K 26/06 | (2014.01) |
| B23K 26/08 | (2014.01) |
| B23K 26/384 | (2014.01) |

(52) U.S. Cl.
CPC .......... *B23K 26/032* (2013.01); *B23K 26/034* (2013.01); *B23K 26/0643* (2013.01); *B23K 26/0648* (2013.01); *B23K 26/0861* (2013.01); *B23K 26/384* (2015.10); *G01N 21/8806* (2013.01); *G02B 17/0808* (2013.01); *G02B 27/141* (2013.01); *G01N 2201/0636* (2013.01); *G01N 2201/06113* (2013.01)

(58) Field of Classification Search
CPC ...... B23K 26/032; B23K 26/04; B23K 26/08; G01N 21/8806; G01N 2201/06113; G01N 2201/0636
USPC .............. 219/121.6, 121.67, 121.68, 121.72, 219/121.75, 121.83
See application file for complete search history.

(56) References Cited

U.S. PATENT DOCUMENTS

| | | | |
|---|---|---|---|
| 4,106,855 A | * | 8/1978 | Coon ................. G02B 17/0808 250/353 |
| 2009/0051834 A1 | * | 2/2009 | Cottier ................... G02B 5/208 349/14 |
| 2013/0134142 A1 | * | 5/2013 | Morikazu .............. B23K 26/00 219/121.75 |

(Continued)

FOREIGN PATENT DOCUMENTS

| | | |
|---|---|---|
| JP | 2010-70388 | 4/2010 |
| JP | 2012-35307 | 2/2012 |
| WO | 2015-036140 A1 * | 3/2015 |

*Primary Examiner* — Thien S Tran
(74) *Attorney, Agent, or Firm* — Oblon, McClelland, Maier & Neustadt, L.L.P.

(57) ABSTRACT

In one embodiment, an optical device having a convex lens, a concave lens and a mirror member is provided. The convex lens is arranged on an axis and has a convex surface at one side in a direction of the axis. The convex lens reflects a first wavelength light and transmits a second wavelength light. The concave lens is arranged on the axis and at the other side in a direction of the axis and having a concave surface. The mirror member has a reflective surface opposing the convex surface and is arranged apart from an outer circumference of the convex lens.

10 Claims, 4 Drawing Sheets

(56) References Cited

U.S. PATENT DOCUMENTS

2015/0371911 A1* 12/2015 McWhirter ............. H01L 22/26
  438/7
2016/0193692 A1* 7/2016 Regaard ............... B23K 26/032
  219/121.62

* cited by examiner

OPTICAL DEVICE AND LASER PROCESSING APPARATUS

CROSS-REFERENCE TO RELATED APPLICATION

This application is based upon and claims the benefit of priority from the prior Japanese Patent Application No. 2015-178598, filed on Sep. 10, 2015, the entire contents of which are incorporated herein by reference.

FIELD

Embodiments described herein relate generally to an optical device and a laser processing apparatus.

BACKGROUND

A laser processing apparatus which is provided with a laser oscillator, a support table and an optical system is known. In laser processing apparatus, the laser oscillator oscillates a laser beam, the support table supports a work, and the optical system guides the laser beam to a processing point of the work. It is also known that defects of an processed product can be detected by detecting processing accuracy in a laser processing using such a laser processing apparatus.

A product inspection can be performed off-line by extracting part of the processed products from a processing line of a laser processing and observing shapes etc. of the part of the extracted processed products with a measuring instrument provided separately.

A processing apparatus which enables an inspection on-line is also known. In the processing apparatus, optical paths of a laser beam for processing and a visible light for measurement are arranged on the same axis so that an optical system for processing and an optical system for measurement are combined. In this case, measurement accuracy may lower in the optical system for measurement due to variation of a distance from a lens for laser processing to a work.

BRIEF DESCRIPTION OF THE FIG.S

DETAILED DESCRIPTION

Figure 1:
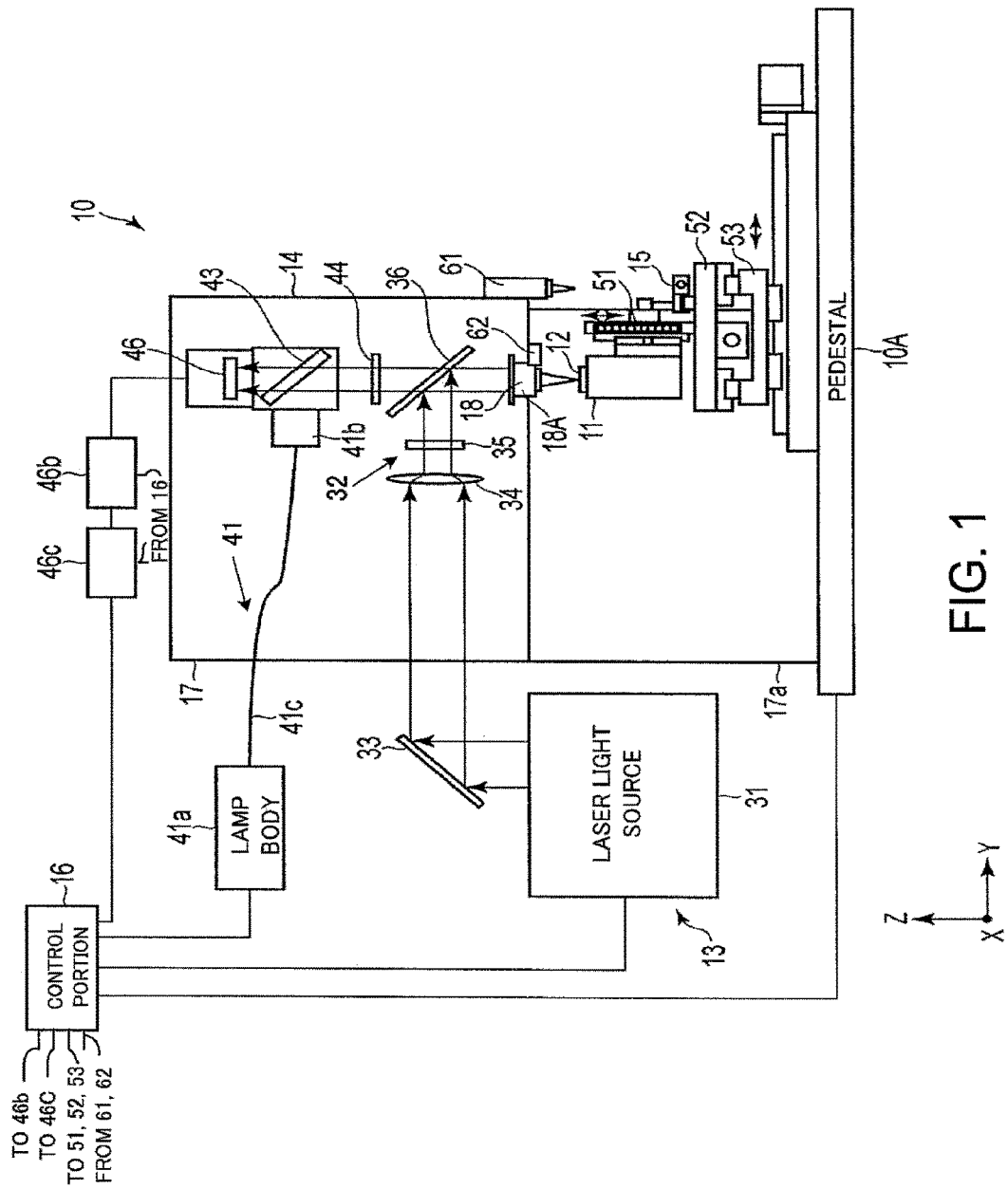
FIG. 1 is an explanatory view showing a configuration of a laser processing apparatus according to an embodiment.

An optical device according to one embodiment has a convex lens, a concave lens and a mirror member. The convex lens is arranged on an axis and has a convex surface at one side in a direction of the axis. The convex lens reflects a first wavelength light and transmits a second wavelength light. The concave lens is arranged on the axis and at the other side in a direction of the axis and having a concave surface. The mirror member has a reflective surface opposing the convex surface and is arranged apart from an outer circumference of the convex lens.

Hereinafter, further embodiments will be described with reference to the drawings. In the drawings, the same reference numerals denote the same or similar portions respectively.

Hereinafter, an optical device, a laser processing apparatus and a laser processing method according to an embodiment will be explained with reference to FIGS. 1 to 3.

FIG. 1 is an explanatory view showing a configuration of a laser processing apparatus according to a first embodiment schematically. FIG. 2 is an explanatory view showing a configuration of an optical system. FIG. 3 is an explanatory view showing a configuration of the optical device and paths of a visible light and a laser beam. In each figure, arrows X, Y and Z shows three directions which intersect perpendicularly to one another, respectively. Each figure may be illustrated such that a configuration is enlarged, reduced or omitted, for explanatory convenience.

Figure 2:
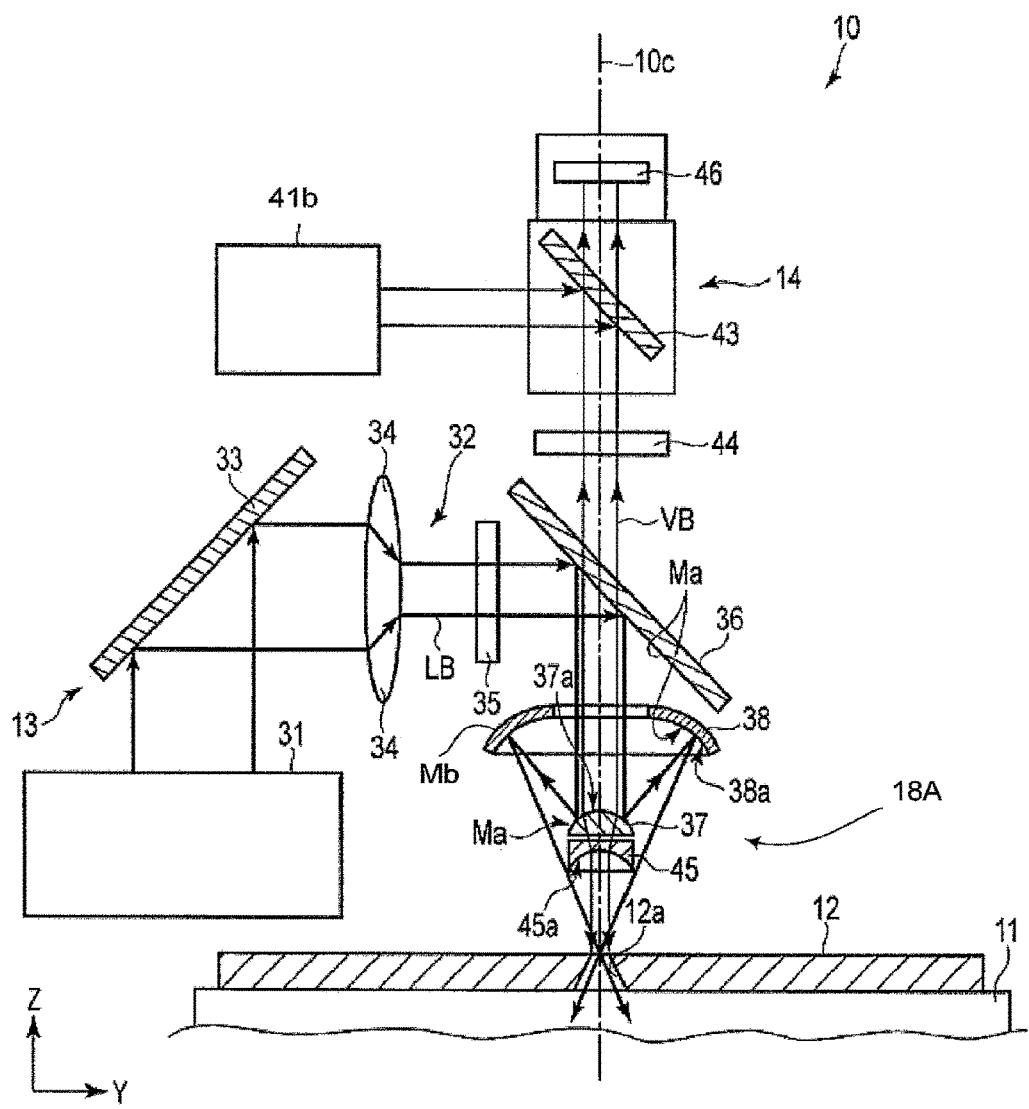
FIG. 2 is an explanatory view showing a configuration of an optical system including an optical device in the laser processing apparatus.

As shown in FIGS. 1, 2, a laser processing apparatus 10 is provided with a stage 11, a processing portion 13, an observing portion 14, a moving portion 15, a lamp body 41a and a control portion 16 which controls these portions. A work 12 which is an object to be processed is mounted on the stage 11, and the stage 11 functions as a supporting portion. The observing portion 14 acquires an image of a processing point of the work 12 using a visible light which is a first wavelength light. The processing portion 13 irradiates a processing point of the work 12 mounted on the stage 11 with a laser beam LB which is a second wavelength light. The moving portion 15 enables movement of the stage 11 respectively in X-axis, Y-axis and Z-axis directions. The lamp body 41a is provided in an exterior of an optical box 17.

The stage 11 is rectangular when the stage 11 is seen from above. The stage 11 is provided with a holding device (not shown) which fixes and holds the work 12 when the work 12 is mounted on the stage 11. An air adsorption mechanism etc. may be used for the holding device 11.

The processing portion 13 is provided with a laser light source 31, a first reflective mirror 33, a condenser lens 34, a laser light mask 35, a separation mirror 36, a convex separation lens 37 as a convex lens, and a second reflective mirror 38 which is a mirror member. The laser light source 31 outputs the laser beam LB as the second wavelength light. The first reflective mirror 33 reflects the laser beam LB. The condenser lens 34 condenses the laser beam LB. The laser light mask 35 shapes the laser beam LB which passes through the condenser lens 34. The separation mirror 36 has a dielectric multilayered film Ma. This dielectric multilayered film Ma reflects the laser beam LB which passes through the laser light mask 35. The convex separation lens 37 is a separating member which has a dielectric multilayered film Ma. This dielectric multilayered film Ma reflects the laser beam LB which is deflected by the separation mirror 36. The second reflective mirror 38 has a dielectric multilayered film Ma which reflects and deflects the laser beam LB reflected by the convex separation lens 37.

Laser light source 31 radiates the laser beam LB towards the first reflective mirror 33. In FIG. 1, the laser light source 31 is arranged in an exterior of the optical box 17 in which a part of a laser optical system 32 is provided. As shown in FIG. 2, the laser light source 31 outputs laser beam LB toward the first reflective mirror 33 upwardly, from a position which is located apart from the first optical axis 10c in a side direction. The laser beam LB may be laser beams of various wavelengths such as a 308 nm XeCL laser beam, a 248 nm KrF excimer laser light, a 193 nm ArF laser beam and a 157 nm F2 laser beam. In the embodiment, the laser light source 31 outputs Krf excimer laser light of a 248 nm wavelength.

The first reflective mirror 33 has a reflective surface which inclines with respect to the laser beam LB radiated from the laser light source 31. The first reflective mirror 33 reflects the laser beam from the laser light source 31 towards the condenser lens 34 arranged in the Y direction, i.e. in a right side direction.

The condenser lens 34 condenses the laser beam LB and guides the laser beam LB towards the laser light mask 35.

The laser light mask 35 removes circumferential light of the laser beam LB having a low energy density which passes through the condenser lens 34. By removal of the circumferential light, the laser light mask 35 shapes a beam form of the laser beam LB, and guides the shaped laser beam LB towards the separation mirror 36.

In FIG. 2, the separation mirror 36 is composed of a material which can transmit the visible light VB as the first wavelength light, and is arranged on the first optical axis 10c along the Z direction. The separation mirror 36 inclines with respect to the first optical axis 10c and the laser light mask 35, and has a surface which opposes the laser light mask 35. A surface of the separation mirror 36 is coated with a dielectric multilayered film Ma which can transmit the visible light VB while reflecting the laser beam LB. The separation mirror 36 reflects the laser beam LB as the second wavelength light while transmitting the visible light VB as the first wavelength light. The separation mirror 36 reflects and refracts the laser beam LB which goes from a direction opposite to the Y direction i.e. from the right side direction to guide the laser beam LB so that the laser beam LB has the same axle as the visible light VB. The separation mirror 36 guides the visible light VB from a down side to the Z direction i.e. to an upper side, for observation, while transmitting the visible light VB which progresses from a lamp body 41a to an irradiation portion 41b to guide the visible light VB in a direction opposite to the Z direction i.e. from the upper side to the down side, for illumination. The irradiation portion 41b is arranged in the optical box 17.

The convex separation lens 37 is a convex lens arranged on the first optical axis 10c and in the Y direction i.e. at the upper side of the stage 11. An convex surface 37a of the convex separation lens 37 is positioned to face in the Y direction i.e. to face the upper side. A dielectric multilayered film Ma is coated on the convex surface 37a of the convex separation lens 37. The convex separation lens 37 transmits light of the first wavelength light and reflects light of the second wavelength light. In more detail, the convex separation lens 37 reflects the laser beam LB which goes from the upper side in the direction opposing the Z direction along the first optical axis 10c, obliquely upward and outward, by the dielectric multilayered film Ma. The convex separation lens 37 guides the visible light VB from the down side to the upper side for illumination while refracting to converge and letting through a large portion of the visible light VB which progresses downward along the Z direction from the upper side.

The second reflective mirror 38 is ring-shaped and has a concave surface 38a which opposes the convex surface 37a of the convex separation lens 37. An opening is formed at a position right above the convex separation lens 37. The second reflective mirror 38 is provided to surround an entire circumference of the first optical axis 10c. The second reflective mirror 38 is arranged so that the second reflective mirror 38 surrounds the first optical axis 10c with a distance kept from the first optical axis 10c. The concave surface 38a of the second reflective mirror 38 which is curved and formed at an inner side is coated with a dielectric multilayered film Ma. An outer surface of the second reflective mirror 38 i.e. a surface at an side opposite to the concave surface 38a is coated with a visible light absorption layer Mb which absorbs the visible light VB.

The second reflective mirror 38 reflects the laser beam LB which is deflected from the first optical axis 10c obliquely upward and outward by the convex separation lens 37. By the reflection of the laser beam LB, the laser beam LB is deflected and guided downward and to an inner side so that the laser beam LB is directed to a processing point positioned downward from the convex separation lens 37. The second reflective mirror 38 lets a part of the visible light VB through the opening. The second reflective mirror 38 absorbs another part of the visible light VB which enters into the circumference of the opening in the visible light absorption layer Mb formed at a back side of the second reflective mirror.

The observing portion 14 has the irradiation portion 41b mentioned above, a half mirror 43, a laser beam attenuating filter 44, the concave lens 45, and the imaging portion 46. The half mirror 43 reflects the visible light VB from the irradiation portion 41b and deflects the visible light VB toward the processing point. The laser beam attenuating filter 44 decreases the laser beam LB. The concave lens 45 is arranged on a work side of the convex separation lens 37. The imaging portion 46 is arranged above the half mirror 43.

The illumination system 41 is provided with the lamp body 41a and the irradiation portion 41b respectively described above, an optical fiber 41c which connects the lamp body 41a and the irradiation portion 41. The irradiation portion 41b is a port to hold an end portion of the optical fiber 41c vertically to an optical tube including the half mirror 43 and the imaging portion 46. The irradiation portion 41b radiates the visible light VB towards the half mirror 43 arranged on the first optical axis 10c and on a right side of the irradiation portion 41b.

The half mirror 43 is arranged on the first optical axis 10c and above the processing position of the stage 11. The half mirror 43 has a reflective surface which inclines toward lower right and is directed to a lower left direction.

The laser beam attenuating filter 44 transmits the visible light VB among incident lights and absorbs the laser beam LB. The laser beam attenuating filter 44 is arranged between the half mirror 43 and the work 12 respectively arranged on the first optical axis 10c.

In FIG. 2, the concave lens 45 as a correcting member has a concave surface 45a which is formed on a side of the work 12 and recessed at a center. The concave lens 45 is arranged between the convex separation lens 37 and the work 12 directly below the convex separation lens 37 on the first optical axis 10c. The concave lens 45 is arranged at a position outside the light path of the laser beam LB i.e. a dead angle portion of the laser beam LB. Specifically, the laser beam LB is reflected at the convex surface 37a of the convex separation lens 37 so that the laser beam LB goes outside the first optical axis 10c. Further, the laser beam LB is guided to a light path to concentrate to the processing point of the work 12 by the second reflective mirror 38. In this case, since the concave lens 45 is arranged close to a back side surface i.e. a lower surface of the convex separation lens 37, the concave lens 45 is placed at a position where the laser beam LB does not reach. The concave lens 45 directs the visible light VB which is refracted by entering into the convex separation lens 37 to pass through the convex separation lens 37, to the work 12. Further, the visible light reflected at the work 12 goes via the concave lens 45 to the convex separation lens 37 to refract the visible light in an opposite direction, and is guided in parallel to the Z direction again.

The imaging portion 46 is arranged on the first optical axis 10c and above the half mirror 43. The imaging portion 46 acquires an image of a processing portion of the work 12 located below by turning on and off the imaging portion 46 at a predetermined timing according to control of the control portion 16. The imaging portion 46 is provided with an imaging sensor such as a CCD imaging sensor or a CMOS imaging sensor, and outputs image data corresponding to incident visible light. The imaging portion 46 is connected to the control portion 16 via an image processing device 46b and a computer 46c for image processing, as shown in FIG. 1. The image data acquired in the imaging portion 46 is transmitted to the image processing device 46b and the computer 46c.

In the laser processing apparatus 10, the processing portion 13 is composed of the condenser lens 34, the laser light mask 35 and the separation mirror 36, and the observing portion 14 is composed of the half mirror 43, the laser beam attenuating filter 44 and the imaging portion 46. The processing portion 13 and the observing portion 14 are respectively provided and supported at predetermined positions of a space in the optical box 17. As shown in FIG. 1, the optical box 17 is fixed to a pedestal 10A via a leg 17a.

Figure 3:
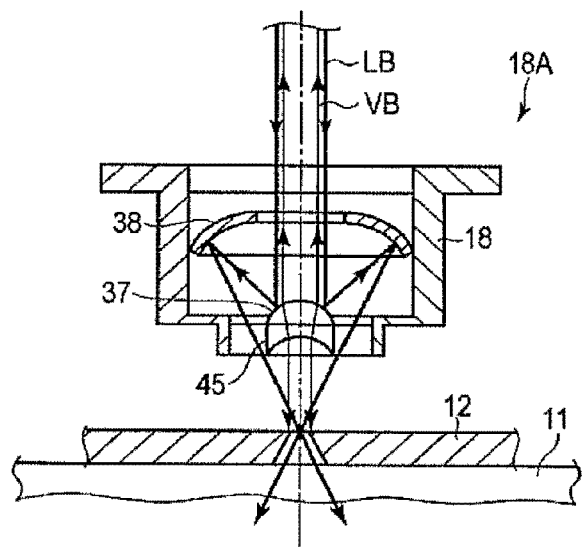
FIG. 3 is an explanatory view showing the configuration of the optical device and paths of a visible light and a laser beam.

As shown in FIG. 3, a cylindrical lens case 18 is fixed to a lower end portion of the optical box 17. The convex separation lens 37, the concave lens 45, and the second reflective mirror 38 are housed in the lens case 18.

The optical device 18A is composed of the lens case 18, the concave lens 45, the second reflective mirror 38 and the convex separation lens 37 provided in the lens case 18.

As shown in FIG. 1, in the laser processing apparatus 10, a laser displacement detector 61 as a position detector and a thermocouple 62 as a temperature detecting element are arranged on an external surface of the optical box 17.

The thermocouple 62 is provided at a position where the temperature of the laser processing apparatus 10 can be detected, for example at a lower end portion of the optical box 17a near the lens case 18. The laser displacement detector 61 is fixed to a side surface of the optical boxes 17. The laser displacement detector 61 is provided with a light receiving portion and a light projecting portion. The laser displacement detector 61 detects light-receipt of a laser beam radiated to the stage 11 so that positional information relating to at least one of the optical device 18A and the stage 11 is detected, and accordingly the distance from the optical device 18A to the stage 11 is measured.

In the embodiment, the laser beam LB and the visible light VB are guided from the different light sources 21, 41a to the common optical axis 10c, and are further separated to be guided to a processing point of the common work 12, using the common optical device 18A. According to the embodiment, the light paths of the laser beam LB and the visible light VB are aligned with each other, and the optical device 18A is shared for processing and observation so that on-line observation which is performed at the processing point is possible.

In FIG. 1, the moving portion 15 is installed on the pedestal 10A. The moving portion 15 is provided with a Z-axis moving mechanism 51, a X-axis moving mechanism 52, and a Y-axis moving mechanism 53. The Z-axis moving mechanism 51 supports the stage 11 and is moved in the Z-axis direction. The X-axis moving mechanism 52 supports the Z-axis moving mechanism 51 and is moved in the X-axis direction. The Y-axis moving mechanism supports the X-axis moving mechanism 52 and is moved in the Y-axis direction. As the Z-axis moving mechanism 51, the X-axis moving mechanism 52, and the Y-axis moving mechanism 53, a linear motor moving mechanism or a feed screw moving mechanism may be used. The linear motor moving mechanism uses a linear motor as a driving source. The feed screw moving mechanism uses a motor for rotating a rotor as a driving source may be used.

The control portion 16 is provided with a microcomputer and a memory portion. The microcomputer controls the stage 11, the processing portion 13, the observing portion 14, the moving portion 15 and lamp body 41a collectively. The memory portion stores various programs, and various information such as position information and temperature information, and processing condition information. A semiconductor memory or a hard disk drive (HDD) can be used for the memory portion.

The control portion 16 performs arithmetic processing based on a program and information, and determines a gap value and a movement amount which are required for position adjustment. The control portion 16 serves as a position controller which controls the moving mechanisms based on a program and information, and positions the stage 11 at a predetermined position. The control portion 16 adjusts a relative positional relationship of the stage 11 and the lens case 18 by moving the stage 11.

The control portion 16 performs processing such as perforating processing by controlling the laser light source 31 of the processing portion 13 and irradiating a processing portion 13 with the laser beam LB at a predetermined timing.

The control portion 16 controls operations of the lamp body 41a and the imaging portion 46 so that the imaging portion 46 can acquire an image of the processing portion at a predetermined timing. The control portion 16 controls the image processing device 46b and the computer 46C based on a program set up beforehand so that, for example, whether or not a processed shape is within a predetermined reference range is detected from an image of the processing portion to perform defect detecting processing.

Hereinafter, an example of a laser processing method according to the embodiment will be explained with reference to FIGS. 1 to 3.

In the example of the laser processing method, a nozzle plate for the use in an ink jet head is used as a work 12. Further, the example shows forming plural rows of nozzle holes for ink discharge in X and Y directions respectively in the nozzle plate, according to ablation processing using a KrF excimer laser.

For preparation before processing, a profile of the surface height of the work 12 is acquired by measuring the position of the work 12 in a Z direction, using the laser displacement detector 61. Further, the surrounding temperature is measured by the thermocouple 62 in order to take a thermal expansion of the laser processing apparatus 10 into consideration in the control portion 16.

The control portion 16 controls the moving portion 15 based on a detected position of the work 12 and a control program stored beforehand. The control portion 16 moves the stage 11 in the X, Y and Z directions to perform positioning to match a processing point to a predetermined position directly below the optical device 18A. At the time, the control portion 16 performs correcting processing to correct a positional relationship in consideration of displacement caused by the influence of thermal expansion of the leg 17a of the optical box 17 and the stage 11 based on a detected temperature. For example, the control portion 16 corrects the relative position of the stage 11 and the lens case 18 by moving stage 11.

After setting the stage 11 to a predetermined position, the control portion 16 controls the laser light source 31 to output a laser beam LB. In FIG. 2, the laser beam LB outputted from the laser light source 31 goes to the first reflective mirror 33, and is reflected and deflected towards the condenser lens 34. The laser beam LB which goes to the condenser lens 34 is condensed and shaped with laser light mask 35. Further, the laser beam LB shaped through the laser light mask 35 is reflected by the separation mirror 36 so that the laser beam LB is deflected to have the same axis as the first optical axis 10c and is guided to the convex separation lens 37 provided downward.

The Laser beam LB which goes to the convex surface 37a of the convex separation lens 37 is reflected by the dielectric multilayered film Ma formed on the convex surface 37a. By the reflection, the laser beam LB is guided towards the second reflective mirror 38 arranged outside and obliquely above so that the laser beam LB is deviated from the first optical axis 10c. The laser beam LB which goes to the second reflective mirror 38 is reflected by the dielectric multilayered film Ma formed on the second reflective mirror 38, and is guided towards the processing point located below on the optical axis 10c. The laser beam LB is focused on the nozzle plate to be processed, and a hole 12a is formed by ablation processing.

At the time, the back side of the convex separation lens 37 is within a dead angle which is deviated from the light path of the laser beam LB. Accordingly, the laser beam LB does not go through the concave lens 45.

On the other hand, the control portion 16 controls operation of the lamp body 41a and the imaging portion 46 at a predetermined timing so that the visible light VB is emitted and that a processed portion of the work 12 is imaged by the imaging portion 46 at a predetermined timing.

The visible light VB is radiated to the half mirror 43 from the irradiation portion 41b. The visible light VB is reflected and deflected downward. The visible light VB is transmitted through the separation mirror 36, and enters into the convex separation lens 37 located below the separation mirror 36. The visible light VB which entered into the convex separation lens 37 is refracted in a convergence direction, and enters into the concave lens 45.

The visible light VB which enters into the concave lens 45 is refracted in a divergent direction so that the visible light VB is again made parallel i.e. telecentric, and is radiated to the work 12 which is the nozzle plate. The radiated visible light VB is reflected at the work 12, and goes through the same light path as an incident light path to the work 12 described above. Further, the visible light VB is again transmitted through the concave lens 45 which is arranged above the work 12, the convex separation lens 37, and the half mirror 43. Further, the visible light VB enters into the imaging portion 46 arranged on the first optical axis 10c.

The control portion 16 operates the image processing device 46a and the computer 46c which are respectively shown in FIG. 1. The image processing device 46a eliminates noise from image data acquired in the imaging portion 46 and binarizes the image data. The computer 46c conducts particle analysis and calculates the diameter of the processed hole 12a. When a calculated diameter is out of a range of a hole specification, the computer 46c judges the processed hole 12a as abnormal in quality. Based on the judgement result, the control portion 16 suspends processing the work 12 i.e. the nozzle plate, and informs the judgement result to a quality control system. The control portion 16 waits for an instruction for starting processing again, or stopping processing.

The optical device 18A, the laser processing apparatus 10 and the laser processing method according to the embodiment can make an optical axis of a visible light VB parallel, by arranging the concave lens 45 capable of deflecting the visible light VB below the concave separation lens 37 through which the visible light VB transmits, and by guiding the visible light VB and a laser beam LB to the same axle. Thus, the work 12 is detectable on-line, and even when distance variation occurs between the work 12 and a CCD camera of the imaging portion 46, a processed shape of the work 12 can be detected with high precision without receiving influence of the distance variation.

For example, when an accuracy specification of the diameter of the processed hole 12a is within a range of a target hole diameter ±1.0 micrometer, it is necessary to stabilize the distance variation between the work 12 and the optical device 18A within ±3 micrometers, in order to realize the accuracy specification. Assuming that the convex separation lens 37 is used but the concave lens 45 is not used in the embodiment, when the distance from the optical device 18A to the work 12 varies by ±3 micrometers, a hole diameter to be imaged varies by ±1.0 micrometer in the case of the numerical aperture (NA) of the convex separation lens 37 is 0.3, and by ±1.7 micrometers in the case of the numerical aperture (NA) of the convex separation lens 37 is 0.5. Accordingly, the hole diameter does not result in an accuracy required to be within the range of the hole specification of ±1.0 micrometer. On the other hand, according to the embodiment, the concave lens 45 is provided to adjust the angle of the visible light VB to become parallel so that the variation range of the hole diameter to be detected can be small and measurement accuracy can be enhanced.

In addition, according to the laser processing apparatus 10 of the embodiment, the position of the concave lens 45 is in a dead angle portion of an optical path of the laser beam LB so that the laser beam LB does not interfere with the concave lens 45. Thus, it is possible to make both measuring a processed shape and processing a work compatible without affecting processing characteristic.

According to the embodiment, the visible light VB can be utilized as illumination for a nozzle plate i.e. a work 12, by using the half mirror 43 in the illumination system 41. Even when a light quantity of a visible light from a processed hole 12a is small, it is possible to image the shape of the processed hole 12a clearly since the visible light from the processed portion of the work 12 is a mirror reflection light.

In the embodiment, a variation of the distance between the optical device 18A and the work 12 arises due to a difference of linear expansion coefficient between the leg 17a of the optical box 17 and the stage 11. An influence on measurement accuracy of the distance due to the variation of the distance can be corrected by taking a displacement caused by temperature change into consideration so that a highly precise processing can be performed.

Figure 4:
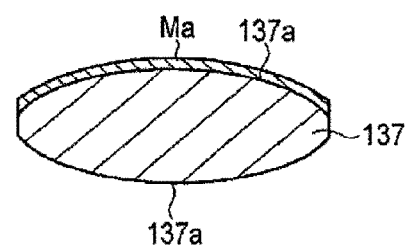
FIG. 4 is a sectional view showing an example of a convex separation lens.
Figure 5:
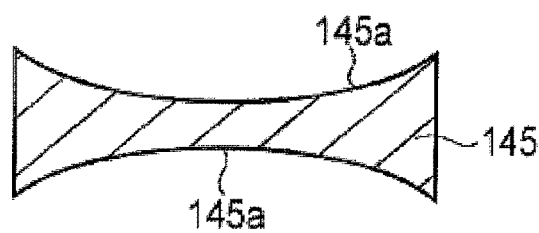
FIG. 5 is a sectional view showing an example of a concave lens.
Figure 6:
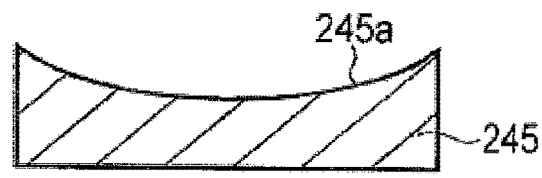
FIG. 6 is a sectional view showing another example of a concave lens.

In the embodiment, the convex separation lens 37 is a lens which is convex only at an upper surface. As shown in FIG. 4, a convex separation lens 137 may be used in place of the convex separation lens 37. The convex separation lens 137 is convex at both upper and lower surfaces 137a respectively, and has a dielectric multilayered film Ma formed only on the upper surface. In the embodiment, the concave lens 45 is a lens which is concave at a lower surface. In place of the concave lens 45, a concave lens 145 shown in FIG. 5 or the concave lens 245 shown in FIG. 6 may be used. The concave lens 145 is concave at both upper and lower surfaces 145a respectively, as shown in FIG. 5. The concave lens 245 is concave only at an upper surface, as shown in FIG. 6.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An optical device for directing a first wavelength light and a second wavelength light guided in one direction along the same axis to an object, the second wavelength light having a second wavelength different from a first wavelength of the first wavelength light, comprising:
   a convex lens which is arranged on the axis and having a convex surface at least at a side opposite to the one direction and which reflects the first wavelength light and transmits the second wavelength light;
   a concave lens arranged on the axis and at a side in the one direction from the convex lens, having a concave surface at least at one side along the axis and transmitting the second wavelength light; and
   a mirror member which has a reflective surface opposing the convex surface and reflects the first wavelength light, the mirror member being arranged at the side opposite to the one direction and apart from an outer circumference of the convex lens and having an opening in a direction of the side opposite to the one direction from the convex lens side, wherein
   the first wavelength light reflected by the mirror member is directed to the object, and
   the second wavelength light transmitted through the convex lens and further through the concave lens is directed to the object and is further reflected at the object so as to be transmitted through the concave lens and further through the convex lens.

2. The optical device according to claim 1, wherein the first wavelength light is a laser beam, the second wavelength light is visible light.

3. The optical device according to claim 1, wherein the convex lens is provided with a dielectric multi-layered film on the convex surface.

4. A laser processing apparatus, comprising:
   an optical device according to claim 1;
   a supporting portion which is arranged on one side of the optical device and supports an object to be processed; and
   an imaging portion which is arranged on another side of the optical device to oppose the object and which detects an image of the object.

5. An apparatus according to claim 4, further comprising a laser light source which generates a laser beam, and a visible light source which generates a visible light.

6. An apparatus according to claim 5, further comprising a separation mirror, wherein the separation mirror is arranged on the axis and reflects the laser beam to guide the laser beam in a direction along the axis, and the separation mirror transmits the visible light.

7. An apparatus according to claim 5, further comprising:
   a position detecting portion which detects position information of at least one of the supporting portion and the optical device; and
   a position adjusting portion which adjusts a relative position of the supporting portion and the optical device based on the position information detected by the position detecting portion.

8. An apparatus according to claim 6, further comprising:
   a position detecting portion which detects position information of at least one of the supporting portion and the optical device; and
   a position adjusting portion which adjusts a relative position of the supporting portion and the optical device based on the position information detected by the position detecting portion.

9. An apparatus according to claim 7, further comprising a temperature detecting portion which detects a temperature of the laser processing apparatus, wherein the position adjusting portion adjusts the relative position of the supporting portion and the optical device based on a detected temperature.

10. An apparatus according to claim 8, further comprising a temperature detecting portion which detects a temperature of the laser processing apparatus, wherein the position adjusting portion adjusts the relative position of the supporting portion and the optical device based on a detected temperature.

* * * * *